(12) United States Patent
Shintre et al.

(10) Patent No.: US 11,775,673 B1
(45) Date of Patent: Oct. 3, 2023

(54) USING PHYSIOLOGICAL CUES TO MEASURE DATA SENSITIVITY AND IMPLEMENT SECURITY ON A USER DEVICE

(71) Applicant: SYMANTEC CORPORATION, Mountain View, CA (US)

(72) Inventors: Saurabh Shintre, Sunnyvale, CA (US); Darren Shou, La Jolla, CA (US)

(73) Assignee: GEN DIGITAL INC., Tempe, AZ (US)

( * ) Notice: Subject to any disclaimer, the term of this patent is extended or adjusted under 35 U.S.C. 154(b) by 1098 days.

(21) Appl. No.: 16/293,446

(22) Filed: Mar. 5, 2019

(51) Int. Cl.
```
G06F 7/04      (2006.01)
H04N 7/16      (2011.01)
G06F 21/62     (2013.01)
G06N 20/00     (2019.01)
A61B 5/0205    (2006.01)
G06F 21/00     (2013.01)
H04L 9/00      (2022.01)
A61B 3/11      (2006.01)
A61B 5/01      (2006.01)
A61B 5/024     (2006.01)
A61B 5/11      (2006.01)
A61B 5/1171    (2016.01)
```
(Continued)

(52) U.S. Cl.
CPC ........ G06F 21/6245 (2013.01); A61B 5/0205 (2013.01); G06F 21/00 (2013.01); G06N 20/00 (2019.01); H04L 9/00 (2013.01); *A61B 3/112* (2013.01); *A61B 5/01* (2013.01); *A61B 5/021* (2013.01); *A61B 5/024* (2013.01); *A61B 5/112* (2013.01); *A61B 5/1176* (2013.01); *A61B 5/443* (2013.01); *A61B 5/4803* (2013.01); *A61B 2503/12* (2013.01); *G06Q 2220/00* (2013.01)

(58) Field of Classification Search
CPC ......... G06F 21/6245; G06F 21/00; H04L 9/00
USPC .......................................................... 726/30
See application file for complete search history.

(56) References Cited

U.S. PATENT DOCUMENTS

| | | | |
|---|---|---|---|
| 7,391,331 B1 * | 6/2008 | Light ................. | G06Q 10/10 340/572.1 |
| 2014/0059066 A1 * | 2/2014 | Koloskov ............. | G06F 16/40 361/679.01 |

(Continued)

OTHER PUBLICATIONS

Luke Stark; "The Emotional Context of Information Privacy"; The Information Society, 32:1, 14-27; 2016; DOI: 10.1080/01972243. 2015.1107167; 15 pages.

(Continued)

*Primary Examiner* — Brandon Hoffman
*Assistant Examiner* — Samuel Ambaye
(74) *Attorney, Agent, or Firm* — MASCHOFF BRENNAN

(57) ABSTRACT

Using physiological cues to measure data sensitivity and implement security on a user device. The method may include obtaining data associated with a first physiological state of a user engaged in a first activity on a user device, obtaining data associated with a second physiological state of the user engaged in a second activity on the user device, where the second activity is determined to be more sensitive to the user than the first activity, and where the second physiological state indicates the user's emotional response to the second activity, and implementing a security action on the user device based on the second physiological state of the user engaged in the second activity.

20 Claims, 3 Drawing Sheets

(51) Int. Cl.
 *A61B 5/00* (2006.01)
 *A61B 5/021* (2006.01)

(56) References Cited

U.S. PATENT DOCUMENTS

| | | | | |
|---|---|---|---|---|
| 2014/0161421 A1* | 6/2014 | Shoemaker | ............ | G06T 7/0016 |
| | | | | 386/278 |
| 2015/0150074 A1* | 5/2015 | Nolan | .................... | H04L 63/10 |
| | | | | 726/1 |
| 2017/0148240 A1* | 5/2017 | Kovacs | ................. | G01G 23/36 |

OTHER PUBLICATIONS

Han Li, Xin (Robert) Luo, Jie Zhang, Heng Xu; "Resolving the privacy paradox: Toward a cognitive appraisal and emotion approach to online privacy behaviors"; 2017; located at: http://www.unm.edu/~xinluo/papers/IM2017.pdf; accessed on Mar. 5, 2019; 11 pages.

Alessandro Acquisti (CMU), Laura Brandimarte (CMU), and Jeff Hancock (Cornell); "Online Self-Disclosure and Offline Threat Detection"; 2015; located at: https://www.econinfosec.org/archive/weis2015/papers/WEIS_2015_acquisti_backup.pdf; accessed on Mar. 5, 2019; 30 pages.

U.S. Appl. No. 15/583,410, filed May 1, 2017, titled "Systems and Methods for Classifying Electronic Files", 60 pages.

\* cited by examiner

USING PHYSIOLOGICAL CUES TO MEASURE DATA SENSITIVITY AND IMPLEMENT SECURITY ON A USER DEVICE

BACKGROUND

With the proliferation of interconnected computer devices collecting personal information from users, the concepts of security and privacy are becoming more important. Research has shown that a person engaging in sensitive or private actions experiences different emotions than when engaging in non-sensitive or public behavior, even if the actions are being experienced passively. In addition, data or activities that are considered private by one person may not be considered private by another person. Thus it may be difficult to measure or define private data or private activities. Concepts like differential privacy may relate only to specific applications (e.g., the privacy of data records in a database) and may not contextualize the sensitivity of the same set of data having different privacy sensitivities in varying settings.

The subject matter claimed herein is not limited to embodiments that solve any disadvantages or that operate only in environments such as those described above. Rather, this background is only provided to illustrate one example technology area where some embodiments described herein may be practiced.

SUMMARY

In some embodiments, a computer-implemented method for using physiological cues to measure data sensitivity and implement security on a user device may be performed by a computer device including one or more processors. The method may include obtaining data associated with a first physiological state of a user engaged in a first activity on a user device, obtaining data associated with a second physiological state of the user engaged in a second activity on the user device, where the second activity is determined to be more sensitive to the user than the first activity, and where the second physiological state indicates the user's emotional response to the second activity, and implementing a security action on the user device based on the second physiological state of the user engaged in the second activity.

In some embodiments, the method may include training a machine learning model on the data obtained when the user is engaged in the first activity to determine a baseline physiological state of the user.

In some embodiments, the method may include training a machine learning model on the data obtained when the user is engaged in the second activity to determine the user's emotional response to the second activity.

In some embodiments, the obtaining of the data associated with the first or second physiological state may include obtaining the data by way of a sensor in electronic communication with the user device, a camera in electronic communication with the user device, or a microphone in electronic communication with the user device, or a combination thereof.

In some embodiments, the obtaining of the data associated with the first physiological state of the user engaged in the first activity may further include obtaining the data while the user is engaged in the first activity on the user device that the user deems safe.

In some embodiments, the obtaining of the data associated with the second physiological state of the user engaged in the second activity may further include obtaining the data while the user is engaged in the second activity on the user device that the user deems private.

In some embodiments, the obtaining of the data associated with the first physiological state of the user may further include obtaining the user's default heart rate, blood pressure, facial expressions, gait, pupil size, skin moisture, body temperature, voice pitch, voice speed, voice volume, or body movements, or a combination thereof.

In some embodiments, the obtaining of the data associated with the second physiological state of the user may further include determining a change from the user's default heart rate, blood pressure, facial expressions, gait, pupil size, skin moisture, body temperature, voice pitch, voice speed, voice volume, or body movements, or a combination thereof.

In some embodiments, the implementing of the security action on the user device may further include dimming a brightness setting of a display of the user device, blurring a portion of the display of the user device, adjusting a volume of the user device, hiding a portion of the display of the user device, or adjusting a font of characters displayed on the user device, or a combination thereof.

In some embodiments, the method may further include removing the security action from the user device. The removing of the security action from the user device may further include removing the security action from the user device after the expiration of a pre-determined time period for implementation of the security action. In some embodiments, the removing of the security action from the user device may further include obtaining data associated with a third physiological state of the user, where the third physiological state of the user satisfies a pre-determined recovery threshold of the user's emotional response. In some embodiments, the removing of the security action may further include determining the user has requested the security action be removed by way of a motion gesture, a verbal keyword, or pressing at least one button on the user device, or a combination thereof.

In some embodiments, a computer device may include a processor, a memory in electronic communication with the processor, and instructions stored in the memory, with the instructions being executable by the processor to perform a method for using physiological cues to measure data sensitivity and implement security on a user device.

In some embodiments, one or more non-transitory computer-readable media may include one or more computer-readable instructions that, when executed by one or more computing devices, cause the one or more computing devices to perform a method for using physiological cues to measure data sensitivity and implement security on a user device.

It is to be understood that both the foregoing summary and the following detailed description are explanatory and are not restrictive of the invention as claimed.

BRIEF DESCRIPTION OF THE DRAWINGS

Embodiments will be described and explained with additional specificity and detail through the use of the accompanying drawings in which.

DETAILED DESCRIPTION

A person's sensitivity to privacy and security increases when he feels the presence of another person, whether directly or indirectly. For example, if a person is looking at sensitive data on a user device, such as personal financial data, the person's sensitivity to the privacy of the data may be increased if he feels or sees another person walking nearby or walking towards him, the sound of a door opening or closing, the sound of footsteps, the smell of another person, etc. The person's physiological response may manifest itself by increased heart rate, sweat, change in facial expressions, increased breathing, etc.

In response to these physiological changes, the person may try to protect the privacy of the data being presented on his device by shifting the position of himself to block a display of the device, closing a display of the device (such as a laptop display) completely or slightly to block a view of the display, physically dimming a display of a device or minimizing a window on a display of a device, turning off sound on a device, etc. Thus, there may be a connection between a person's physiological reactions to the presence of another person, and the person's behavior when engaging in sensitive activities on a user device.

In many, if not all cases, a person's expected rational behavior may not be in line with what a person's brain perceives. Thus, even if a person may think he is not sensitive to the presence of another person, the person's physiology may change regardless, indicating a subconscious sensitivity. Thus, the embodiments disclosed herein may detect physiological changes in a person with regard to a set of a data in a specific time, and may automatically implement a security action on a user device based on the detection of the physiological changes.

Figure 1:
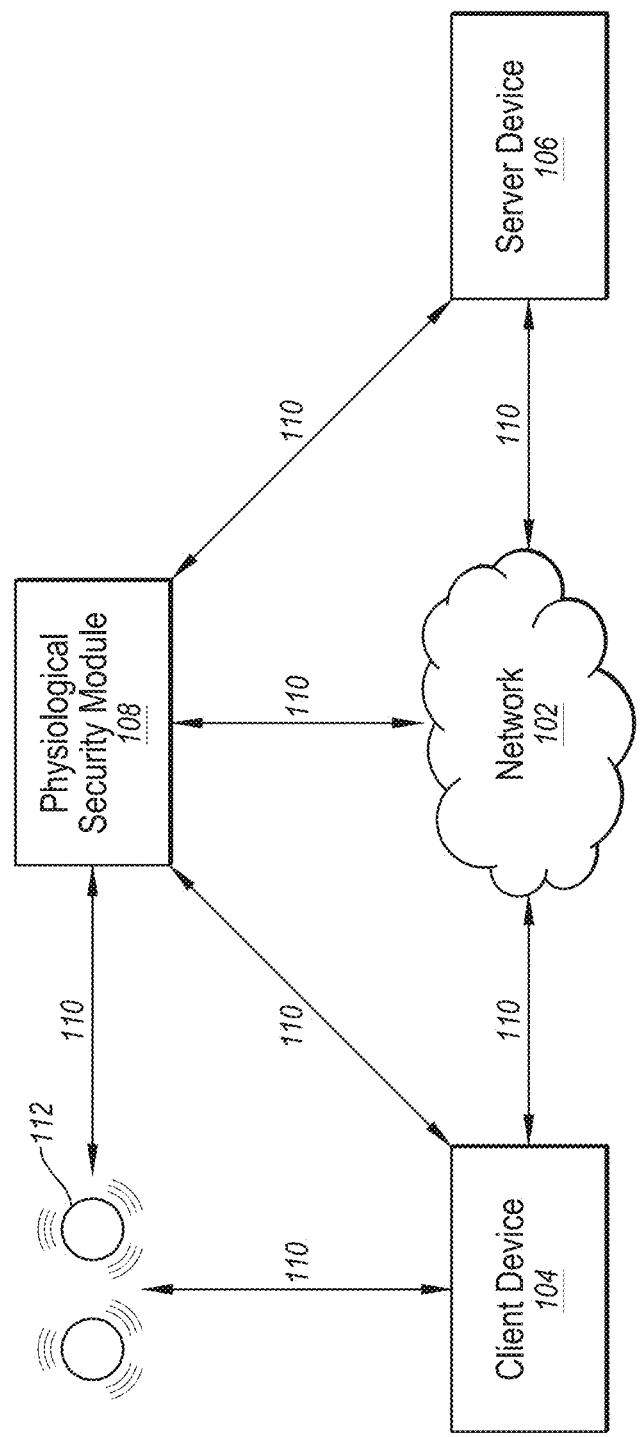
FIG. 1 illustrates an example system configured for using physiological cues to measure data sensitivity and implement security on a user device.

Turning to the figures, FIG. 1 illustrates an example system 100 configured for using physiological cues to measure data sensitivity and implement security on a user device. The system 100 may include a network 102, a client device 104, a physiological security module 108, a server device 106, and sensor(s) 112. In some embodiments, the physiological security module 108 may be a software module executing on a standalone device that communicates with the client device 104 and/or the server device 106. In an alternative or additional embodiment, the physiological security module 108 may be part of the client device 104 and/or the server device 106.

In some embodiments, the network 102 may be configured to communicatively couple the client device 104 and the server device 106, and in some embodiments, the physiological security module 108 and/or the sensor(s) 112. In some embodiments, the network 102 may be any wired or wireless network, or combination of multiple networks, configured to send and receive communications between systems and devices by way of example communication links 110. In some embodiments, the network 102 may include a Personal Area Network (PAN), a Local Area Network (LAN), a Metropolitan Area Network (MAN), a Wide Area Network (WAN), a Storage Area Network (SAN), the Internet, or some combination thereof. In some embodiments, the network 102 may also be coupled to, or may include, portions of a telecommunications network, including telephone lines, for sending data in a variety of different communication protocols, such as a cellular network or a Voice over IP (VoIP) network.

Figure 3:
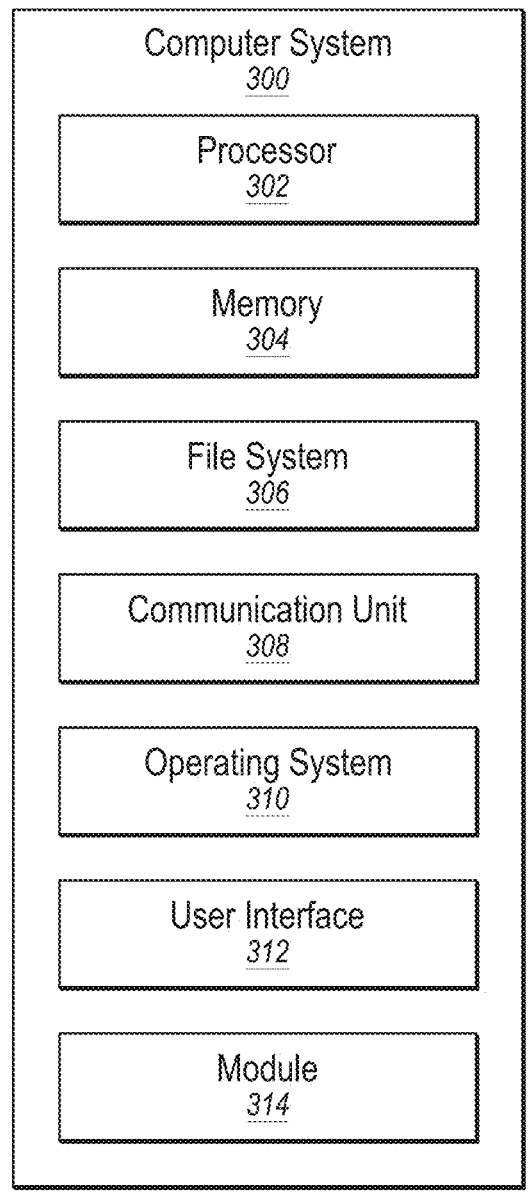
FIG. 3 illustrates an example computer system that may be employed in using physiological cues to measure data sensitivity and implement security on a user device.

In some embodiments, the client device 104 may be a computer system capable of communicating over the network 102 and capable of, at least, detecting physiological elements and changes of a person and implementing a security feature on a computer device, examples of which are disclosed herein in connection with the computer system 300 of FIG. 3. In some embodiments, the client device 104 may be a computer device, such as a smartphone, desktop computer, laptop computer, control system, tablet, computer wearable device, etc. A person may herein be referred to as a "user," as many of the example embodiments are in the context of interactions with a user device which may be a computer device.

Sensor(s) 112 may be a stand-alone sensor in communication with client device 104 and/or physiological security module 108, or may be integrated within client device 104 and/or physiological security module 108. Sensor(s) 112 may include, but is not limited to, a biometric sensor (e.g., fingerprint, facial recognition, iris recognition, retinal recognition, palm recognition, voice recognition, gait sensor, etc.), a thermometer, an infrared sensor, an accelerometer, a gyroscope, a microphone, a camera, etc.

In some embodiments, the server device 106 may be any computer system capable of communicating over the network 102 with client device 104. In some embodiments, the server device 106 may communicate with the client device 104 through communications with physiological security module 108. Examples of the server device 106 are disclosed herein in connection with the computer system 300 of FIG. 3.

In some embodiments, the physiological security module 108 may be implemented in conjunction with any threat based security application such as FIREGLASS®, owned by SYMANTEC® Corporation.

Modifications, additions, or omissions may be made to the system 100 without departing from the scope of the present disclosure. For example, in some embodiments, the system 100 may include additional components similar to the components illustrated in FIG. 1 that each may be configured similarly to the components illustrated in FIG. 1. Further, it is understood that the communication links 110 between the components illustrated in FIG. 1 (illustrated as left-right arrows) may be part of the network 102 or another network.

Physiological security module 108 may obtain data related to physiological behaviors of a user in a variety of situations using, for example, sensor(s) 112. A user may exhibit certain physiological behaviors based on what the user is doing a specific point in time, where the user is, who the user is with, and the safety of the actions and/or locations where "safety" may be related to the sensitivity of the action (e.g., looking at private data), the safety of a location (e.g., a home versus a dark alleyway), the type of company (e.g., alone or with a trusted person versus with strangers or someone threatening), etc.

Thus, a user's physiological behaviors may indicate a sense of security when engaging in certain activities (e.g., on the client device 104) in a specific location, and/or with specific company, but the user's physiological behaviors may shift if the user experiences a change in that sense of security while engaging in those same activities. For example, if the user is looking at a private document on the client device 104 alone and another person walks into the room, the user may become nervous and want to shield the private document from the new person. Thus, a security action may be implemented by the physiological security module 108 in order to provide the user with a preemptive sense of security and/or privacy.

For purposes of explanation, in one example, a user may have access to a financial software application (or app), such as may be provided by the user's financial institution. The user may access the financial application using any number of example user devices including, but not limited to, a smartphone, a laptop, a desktop, a tablet, and a smartwatch. Each of these devices may display sensitive information, by way of the financial application, such as names, addresses, phone numbers, Social Security numbers, account numbers, monetary amounts, etc.

In an example embodiment, a user may be sensitive to sharing financial information with strangers, or even with certain people with whom the user does not have a secure relationship. Thus, if the user accesses his financial application at home alone, he may be relaxed and unconcerned with what is being displayed. However, if the user is accessing his financial information and someone walks into the room, the user may experience some stress related to the potential invasion of privacy (whether it is purposeful or incidental) by another person. In addition, if the user is home alone and does not expect that another person is home, the stress the user may feel may be more significant, as the approach of another person comes as a surprise.

In another example, the user may be some place public, such as an airport, but may want to access his financial information using the financial application. The stress a user may feel at accessing this sensitive information may be higher in a crowded public place, than at home or even at work. Thus, the physiological security module 108 may train a machine learning model on a user's default physiological behaviors versus physiological behavior changes based on various types of data, situations, locations, times of day, presence of various people, etc.

Physiological behavior data of a user may be obtained from the sensor(s) 112, or from multiples sensors and sources, including user input. For example, a user may be wearing a computer device that measures and obtains physiological data, such as a smartwatch having sensor(s) 112 that includes an accelerometer, a thermometer, a heart rate monitor, an oxygen sensor, a microphone, a speaker, a camera, a moisture detector, etc. The sensor(s) 112 may be part of the client device 104 or may be in communication with the client device 104, with the physiological security module 108, with the server device 106, etc. Other sensors may include a camera associated with the client device 104, a microphone or speaker associated with the client device 104, etc.

In training a machine learning model on a user's default physiological behavior, the physiological security module 108 may be trained on the user's obtained physiological data while the user is performing a regular, non-sensitive, non-private activity (e.g., at home, alone, surfing the internet, etc.). Training the model on "regular" activities, or activities in which the user is engaged while feeling no insecure emotions, may provide the physiological security module 108 with a default security baseline for the user.

Default physiological behavior data that is obtained by sensor(s) 112 may include, but is not limited to, a resting or calm heart rate, regular body moisture (e.g., sweat, saliva), eye movement, pupil dilation, breathing rate, exhalations, regular body temperature, micro-expressions, normal body movements, relaxed posture, relaxed gait, etc. The default physiological behavior data that is obtained may be personal to each user, and thus the model may be retrained, and the baseline adjusted, based on additional data obtained or received. For example, a user may have a heart condition and may be on medication to regulate blood pressure such that, even in a stressful situation, the user's blood pressure or heart rate does not increase significantly. However, the physiological security module 108 may be able to detect small granularities in physiological data, such that a user that has a limited range of blood pressure and/or heart rate changes may be enough to indicate an emotional change in the user.

In an additional or alternative embodiment, the physiological security module 108 may determine habits and usage patterns of the user, in addition to physiological behaviors, to improve a baseline. For example, a user may only access his financial application on a desktop computer located at home during a weekday when the user is home sick. Combined with data obtained that indicates the user has a higher than normal temperature, the physiological security module 108 may determine that the user is not stressed while looking at the financial application, but rather is sick. In addition, a user may provide personalized user input to the physiological security module 108 which is personalized to the user (e.g., maximum heart rate).

Because different users may have different ranges of default physiological behaviors, in an additional or alternative embodiment, the physiological security module 108 may apply different weights to various physiological behaviors based on the behaviors observed, user input, etc. For example, if the user has a heart condition, the change in heart rate or blood pressure may impact the determination that a user is experiencing less stress than if the user's pupils dilate and the user's temperature increases.

In one embodiment, the physiological security module 108 may train a machine learning model on a change in physiological behaviors based on the user's emotional response to an event or situation. In one embodiment, the training may be enabled on a change in a physiological behavior when a user is engaged in an activity that would be deemed private or sensitive. In some examples, the activity itself may always or frequently be considered private or sensitive, no matter the location of the user at the time of the activity or the presence of other people at the time of the activity; whereas, in an additional or alternative embodiment, the activity may not be considered sensitive without the addition of another variable, such as location, time, presence of others, or other situations (e.g., the user is in a rush, the user is already nervous about something when engaging in the activity, the user is aware that the activity is not appropriate at this time, etc.).

Example activities that may be deemed private or sensitive may include, but are not limited to, looking at photographs, watching videos, listening to audio, accessing sensitive files or data, communicating with specific people (e.g., on the telephone, over electronic communications), searching for certain topics on the internet, etc. Example activities that may be deemed private or sensitive when the location is a variable may include locations such as public parks, airports, on an airplane, offices, hospitals, on the street, etc.

Training and retraining the machine learning models on the user's default and/or baseline physiological behaviors, as well on the user's responses to activities that may be deemed private or sensitive may be an ongoing and updated process as time passes and as activities or behaviors change.

After the models have begun training, the physiological security module 108 may determine that the user is engaged in an activity that may be deemed private or sensitive. In one embodiment, the determination may be made using any number of techniques including monitoring past behaviors and habits (e.g., times certain applications are accessed, locations at which certain applications are accessed, common people in the user's presence, etc.), data obtained from sensor(s) 112, etc. Thus, in an alternative or additional embodiment, the sensor(s) 112 may obtain other data related to the activity such as the location, the number of people, identifying the people at the location, sounds, smells, time, lighting, etc.

In addition, the physiological security module 108 may determine that the user is experiencing an emotional response to a current activity. The user's emotional response may be captured by determining a change in, for example, micro-expressions, heart rate, skin moisture, temperature, dilation of the pupils, etc. Thus, although a user may not consciously be aware of feeling an increase in sensitivity with regard to his privacy, the determination of physiological changes may determine that the user is in fact, experiencing an emotional response related to the situation, and may likely be feeling stress and the need for increased privacy or security.

In response to determining the change in the user's physiological behavior, the physiological security module 108 may implement a security action to enhance the user's security and/or privacy with regard to the current situation. For example, the security action may include, but is not limited to, dimming the brightness of a display, turning off a display entirely, blurring the display or portions of the display containing sensitive information, minimizing a window, blocking the ability to take a screen capture, disabling a camera associated with the client device 104, disabling a speaker associated with the client device 104, disabling a microphone associated with the client device 104, reducing a font of characters displayed on the client device 104, altering a volume of sound emitted from client device 104, transferring the network connection to a virtual private network (VPN) from a public or shared network, disabling a Wi-Fi or cellular connection, and the like. Other security actions may be contemplated and are not limited to those discussed herein.

In another embodiment, security actions may not be limited to affecting a change on a display of a user device, such as a computing device display, but may be implemented in a different scenario that would benefit from a security action and/or a privacy action, such as dimming the lights in a room, increasing the brightness of the lights in a room, turning down speakers, transmitting an alarm in a vehicle or in a room, etc.

In an additional or alternative embodiment, once a security action has been implemented, the user may wish to return to the pre-altered state through no or minimal efforts. Thus, the security action may persist for a pre-determined period of time, the expiration of which may remove or reverse the security action automatically. In an additional or alternative embodiment, the security action may persist until the physiological security module 108 determines that the user has returned to a less stressful state, where "less stressful" may be determined as having satisfied a pre-determined threshold of physiological behaviors. For example, the pre-determined threshold may be within a few data points of the user's determined default and/or baseline physiological state as determined by the machine learning model.

In an additional or alternative embodiment, the user may affect a change in the security action. For example, if the security action blurred the display due to the presence of another person, the display may unblur once it is determined the user is alone again. In an additional or alternative embodiment, the user may take a proactive action to remove the security action, such as speaking a keyword (e.g., "safe"), pressing a default key on the keyboard, pressing a home button, swiping on a screen, using a hand gesture (e.g., swiping up in the air), shaking a hand-held computing device, moving the device in a specific pattern (e.g., a figure-eight pattern), etc. Where the security action may be removed quickly and easily, the consequence of a false positive may have a minimal effect on the user.

Although unblurring the display is used as an example, removing the security action may include reversing, removing, or otherwise altering any of the contemplated security actions taken by the physiological security module 108.

In one embodiment, actions to reverse, remove, or otherwise alter the security action may be established by default, such as by an administrator of the physiological security module 108. In an additional or alternative embodiment, actions to reverse, remove, or otherwise alter the security action may be established by a user by taking user preferences into consideration.

Figure 2:
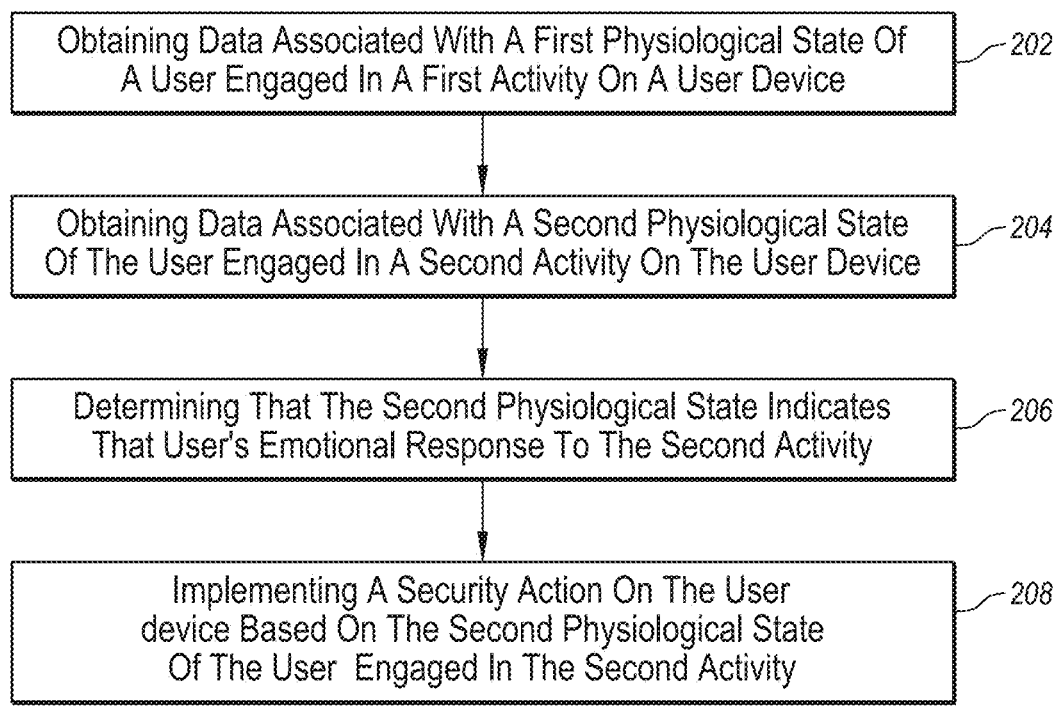
FIG. 2 illustrates an example method for using physiological cues to measure data sensitivity and implement security on a user device.

FIG. 2 illustrates an example method 200 using physiological cues to measure data sensitivity and implement security on a user device. The method 200 may be performed, in some embodiments, by a device or system, such as by the client device 104, the server device 106, and/or the physiological security module 108, operating independently or on one of the other described devices. In these and other embodiments, the method 200 may be performed by one or more processors based on one or more computer-readable instructions stored on one or more non-transitory computer-readable media. The method 200 will now be described in connection with FIGS. 1 and 2.

Method 200 may include, at action 202, obtaining data associated with a first physiological state of a user engaged in a first activity on a user device. For example, the physiological security module 108 may obtain, at action 202, data related to a user's physiological state, using the sensor(s) 112, while the user is engaged in a "regular" activity with the client device 104. A "regular" activity may be when the user is engaged in an activity that the user does not feel is particularly private or where the content being consumed by the user on the client device 104 is not private or does not cause the user to experience an emotional response.

Method 200 may include, at action 204, obtaining data associated with a second physiological state of the user engaged in a second activity on the user device. For example, the physiological security module 108 may obtain, at action 204, data related to the user's physiological state, using the sensor(s) 112, while the user is engaged in an activity that the user believes to be sensitive or private, especially when compared to engaging in the "regular" activity.

Method 200 may include, at action 206, determining that the second activity is more sensitive to the user than the first activity. For example, the physiological security module 108 may determine, at action 206, that this second activity involves is more sensitive to the user because it involves the user looking at private information (e.g., personal information, financial information, confidential information) or it involves the user engaging in an activity that is not appropriate, or is meant to be kept secret or private.

Method 200 may include, at action 208, determining that the second physiological state indicates the user's emotional response to the second activity. For example, the physiological security module 108 may determine, at action 208, that the second physiological state of the user may vary from the first physiological state in that the user has exhibited an emotional change from that exhibited when the user was engaged in the first activity.

Method 200 may include, at action 210, implementing a security action on a user device based on the second physiological state of the user engaged in the second activity. For example, in response to the physiological security module 108 determining that the user is experiencing the second physiological state, the physiological security module 108 may implement, at action 210, a security action on a user device to provide the user with increased privacy or security regarding the second activity.

Although the actions of the method 200 are illustrated in FIG. 2 as discrete actions, various actions may be divided into additional actions, combined into fewer actions, reordered, expanded, or eliminated, depending on the desired implementation. The method 200 may result in the practical application of increasing the security or privacy of an offline or online activity in which the user is engaged on a user device upon automatically determining that the user is exhibiting a need for increased security or privacy. Further, it is understood that the method 200 may improve the functioning of a computer system itself. For example, the method 200 may improve the functionality of a user device itself, such as the client device 104 itself for example, because a security action may be automatically taken to secure the user device when an emotional response of a user indicates that private information is being presented on the user device in a situation that calls for privacy.

FIG. 3 illustrates an example computer system that may be employed in using physiological cues to measure data sensitivity and implement security on a user device. In some embodiments, the computer system 300 may be part of any of the systems or devices described in this disclosure. For example, the computer system 300 may be part of any of the client device 104, the server device 106, and/or the physiological security module 108 of FIG. 1.

The computer system 300 may include a processor 302, a memory 304, a file system 306, a communication unit 308, an operating system 310, a user interface 312, and a module 314, which all may be communicatively coupled. In some embodiments, the computer system may be, for example, a desktop computer, a client computer, a server computer, a mobile phone, a laptop computer, a smartphone, a wearable device (e.g., a smartwatch, heart rate monitor, oxygen detector, thermometer), a tablet computer, a portable music player, a networking device, or any other computer system.

Generally, the processor 302 may include any suitable special-purpose or general-purpose computer, computing entity, or processing device including various computer hardware or software modules and may be configured to execute instructions stored on any applicable computer-readable storage media. For example, the processor 302 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data, or any combination thereof. In some embodiments, the processor 302 may interpret and/or execute program instructions and/or process data stored in the memory 304 and/or the file system 306. In some embodiments, the processor 302 may fetch program instructions from the file system 306 and load the program instructions into the memory 304. After the program instructions are loaded into the memory 304, the processor 302 may execute the program instructions. In some embodiments, the instructions may include the processor 302 performing one or more of the actions of the method 200 of FIG. 2.

The memory 304 and the file system 306 may include computer-readable storage media for carrying or having stored thereon computer-executable instructions or data structures. Such computer-readable storage media may be any available non-transitory media that may be accessed by a general-purpose or special-purpose computer, such as the processor 302. By way of example, and not limitation, such computer-readable storage media may include non-transitory computer- readable storage media including Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage media which may be used to carry or store desired program code in the form of computer-executable instructions or data structures and which may be accessed by a general-purpose or special-purpose computer.

Combinations of the above may also be included within the scope of computer-readable storage media. Computer-executable instructions may include, for example, instructions and data configured to cause the processor 302 to perform a certain operation or group of operations, such as one or more of the actions of the method 200 of FIG. 2. These computer-executable instructions may be included, for example, in the operating system 310, in one or more applications, such as the physiological security module 108 of FIG. 1, or in some combination thereof.

The communication unit 308 may include any component, device, system, or combination thereof configured to transmit or receive information over a network, such as the network 102 of FIG. 1. In some embodiments, the communication unit 308 may communicate with other devices at other locations, the same location, or even other components within the same system. For example, the communication unit 308 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, a cellular communication device, etc.), and/or the like. The communication unit 308 may permit data to be exchanged with a network and/or any other devices or systems, such as those described in the present disclosure.

The operating system 310 may be configured to manage hardware and software resources of the computer system 300 and configured to provide common services for the computer system 300.

The user interface 312 may include any device configured to allow a user to interface with the computer system 300. For example, the user interface 312 may include a display, such as an LCD, LED, or other display, that is configured to present video, text, application user interfaces, and other data as directed by the processor 302. The user interface 312 may further include a mouse, a track pad, a keyboard, a touchscreen, volume controls, other buttons, a speaker, a microphone, a camera, any peripheral device, or other input or output device. The user interface 312 may receive input from a user and provide the input to the processor 302. Similarly, the user interface 312 may present output to a user.

The module 314 may be one or more computer-readable instructions stored on one or more non-transitory computer-readable media, such as the memory 304 or the file system 306, that, when executed by the processor 302, is configured to perform one or more of the actions of the method 200 of FIG. 2. In some embodiments, the module 314 may be part of the operating system 310 or may be part of an application of the computer system 300, or may be some combination thereof. In some embodiments, the module 314 may function as the physiological security module 108 of FIG. 1.

Modifications, additions, or omissions may be made to the computer system 300 without departing from the scope of the present disclosure. For example, although each is illustrated as a single component in FIG. 3, any of the components 302-314 of the computer system 300 may include multiple similar components that function collectively and are communicatively coupled. Further, although illustrated as a single computer system, it is understood that the computer system 300 may include multiple physical or virtual computer systems that are networked together, such as in a cloud computing environment, a multitenancy environment, or a virtualization environment.

As indicated above, the embodiments described herein may include the use of a special purpose or general purpose computer (e.g., the processor 302 of FIG. 3) including various computer hardware or software modules, as discussed in greater detail below. Further, as indicated above, embodiments described herein may be implemented using computer-readable media (e.g., the memory 304 or file system 306 of FIG. 3) for carrying or having computer-executable instructions or data structures stored thereon.

In some embodiments, the different components and modules described herein may be implemented as objects or processes that execute on a computing system (e.g., as separate threads). While some of the methods described herein are generally described as being implemented in software (stored on and/or executed by general purpose hardware), specific hardware implementations or a combination of software and specific hardware implementations are also possible and contemplated.

In accordance with common practice, the various features illustrated in the drawings may not be drawn to scale. The illustrations presented in the present disclosure are not meant to be actual views of any particular apparatus (e.g., device, system, etc.) or method, but are merely example representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, it is understood that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the summary, detailed description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

The foregoing description, for purpose of explanation, has been described with reference to specific embodiments. However, the illustrative discussions above are not intended to be exhaustive or to limit the invention as claimed to the precise forms disclosed. Many modifications and variations are possible in view of the above teachings. The embodiments were chosen and described to explain practical applications, to thereby enable others skilled in the art to utilize the invention as claimed and various embodiments with various modifications as may be suited to the particular use contemplated.

The invention claimed is:

1. A computer-implemented method for using physiological cues to measure data sensitivity and implement security on a user device, at least a portion of the method being performed by a computer device comprising one or more processors, the method comprising:

obtaining data associated with a first physiological state of a user while the user is engaged in a first activity on a user device, wherein the first physiological state of the user is based, at least in part, on the first activity on the user device and the first activity on the user device is a non-sensitive activity that the user deems safe;

obtaining data associated with a second physiological state of the user while the user is engaged in a second activity on the user device;

comparing the first physiological state of the user with the second physiological state of the user to identify a change in the user's physiological state while the user is engaged in the second activity;

determining, based on the change in the user's physiological state while the user is engaged in the second activity, that the second activity is more sensitive to the user than the first activity; and implementing a security action on the user device based on the determination that the second activity is more sensitive to the user than the first activity.

2. The computer-implemented method of claim 1, further comprising:

training a machine learning model on the data obtained while the user is engaged in the first activity to determine a baseline physiological state of the user.

3. The computer-implemented method of claim 1, further comprising:

training a machine learning model on the data obtained while the user is engaged in the second activity to determine the user's emotional response to the second activity.

4. The computer-implemented method of claim 1, wherein the obtaining of the data associated with the first or second physiological state further comprises:

obtaining the data by way of: a sensor in electronic communication with the user device, a camera in electronic communication with the user device, or a microphone in electronic communication with the user device, or a combination thereof.

5. The computer-implemented method of claim 1, wherein the obtaining of the data associated with the second physiological state of the user while the user is engaged in the second activity further comprises:

obtaining the data while the user is engaged in the second activity on the user device that the user deems private.

6. The computer-implemented method of claim 1, wherein the obtaining of the data associated with the first physiological state of the user further comprises:

obtaining the user's: default heart rate, blood pressure, facial expressions, gait, pupil size, skin moisture, body temperature, voice pitch, voice speed, voice volume, or body movements, or a combination thereof.

7. The computer-implemented method of claim 6, wherein the comparing of the first physiological state of the user with the second physiological state of the user to identify a change in the user's physiological state while the user is engaged in the second activity further comprises:

determining a change from the user's: default heart rate, blood pressure, facial expressions, gait, pupil size, skin moisture, body temperature, voice pitch, voice speed, voice volume, or body movements, or a combination thereof.

8. The computer-implemented method of claim 1, wherein the implementing of the security action on the user device further comprises:

dimming a brightness setting of a display of the user device, blurring a portion of the display of the user device, adjusting a volume of the user device, hiding a portion of the display of the user device, or adjusting a font of characters displayed on the user device, or a combination thereof.

9. The computer-implemented method of claim 1, further comprising:

removing the security action from the user device.

10. The computer-implemented method of claim 9, wherein the removing of the security action from the user device further comprises:

removing the security action from the user device after expiration of a pre-determined time period for implementation of the security action.

11. The computer-implemented method of claim 9, wherein the removing of the security action from the user device further comprises:

obtaining data associated with a third physiological state of the user, wherein the third physiological state of the user satisfies a pre-determined recovery threshold from the user's second physiological state.

12. The computer-implemented method of claim 9, wherein the removing of the security action further from the user device comprises:

determining the user has requested the security action be removed by way of: a motion gesture, a verbal keyword, or pressing at least one button on the user device, or a combination thereof.

13. One or more non-transitory computer-readable media comprising one or more computer readable instructions that, when executed by one or more processors of a computing device, cause the computing device to perform a method for using physiological cues to measure data sensitivity and implement security on a user device, the method comprising:

obtaining data associated with a first physiological state of a user while the user is engaged in a first activity on a user device, wherein the first physiological state of the user is based, at least in part, on the first activity on the user device and the first activity on the user device is a non-sensitive activity that the user deems safe;

obtaining data associated with a second physiological state of the user while the user is engaged in a second activity on the user device;

comparing the first physiological state of the user with the second physiological state of the user to identify a change in the user's physiological state while the user is engaged in the second activity;

determining, based on the change in the user's physiological state while the user is engaged in the second activity, that the second activity is more sensitive to the user than the first activity; and implementing a security action on the user device based on the determination that the second activity is more sensitive to the user than the first activity.

14. The non-transitory computer-readable media of claim 13, wherein the method further comprises:

training a machine learning model on the data obtained while the user is engaged in the first activity to determine a baseline physiological state of the user.

15. The non-transitory computer-readable media of claim 13, wherein the method further comprises:

training a machine learning model on the data obtained while the user is engaged in the second activity to determine the user's emotional response to the second activity.

16. The non-transitory computer-readable media of claim 13, wherein the obtaining of the data associated with the second physiological state of the user further comprises:

obtaining the data by way of: a sensor in electronic communication with the user device, a camera in electronic communication with the user device, or a microphone in electronic communication with the user device, or a combination thereof.

17. The non-transitory computer-readable media of claim 13, wherein the method further comprises:
removing the security action from the user device.

18. A system for using physiological cues to measure data sensitivity and implement security, comprising:
a processor;
a memory in electronic communication with the processor; and
instructions stored in the memory, the instructions being executable by the processor to:
obtain data associated with a first physiological state of a user while the user is engaged in a first activity on a user device, wherein the first physiological state of the user is based, at least in part, on the first activity on the user device and the first activity on the user device is a non-sensitive activity that the user deems safe;
obtain data associated with a second physiological state of the user while the user is engaged in a second activity on the user device;
compare the first physiological state of the user with the second physiological state of the user to identify a change in the user's physiological state while the user is engaged in the second activity;
determine, based on the change in the user's physiological state while the user is engaged in the second activity, that the second activity is more sensitive to the user than the first activity;
implement a security action on the user device based on the determination that the second activity is more sensitive to the user than the first activity; and
remove the security action from the user device after a pre-determined criteria is satisfied.

19. The computer-implemented method of claim 1, wherein the first activity is deemed safe based on either a nonprivate nature of data displayed on the user device or a location of the user during the first activity.

20. The non-transitory computer-readable media of claim 13, wherein the first activity is deemed safe based on either a nonprivate nature of data displayed on the user device or a location of the user during the first activity.

* * * * *